(12) United States Patent
Braunschweig et al.

(10) Patent No.: US 9,206,180 B2
(45) Date of Patent: Dec. 8, 2015

(54) SUPERSTRUCTURES OF DIKETOPYRROLOPYRROLE DONORS AND PERYLENEDIIMIDE ACCEPTORS FORMED BY HYDROGEN-BONDING AND π•••π STACKING

(71) Applicant: New York University, New York, NY (US)

(72) Inventors: Adam B. Braunschweig, Miami, FL (US); Stephen Rieth, Burke, VA (US); Zhong Li, Smithtown, NY (US); Charlotte E. Hinkle, Burke, VA (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 14/187,737

(22) Filed: Feb. 24, 2014

(65) Prior Publication Data
US 2014/0243531 A1    Aug. 28, 2014

Related U.S. Application Data

(60) Provisional application No. 61/768,973, filed on Feb. 25, 2013.

(51) Int. Cl.
*C07D 471/06*    (2006.01)

(52) U.S. Cl.
CPC .................................... *C07D 471/06* (2013.01)

(58) Field of Classification Search
CPC .................................................. C07D 471/06
USPC ..................................... 548/453, 466; 546/37
See application file for complete search history.

(56) References Cited

U.S. PATENT DOCUMENTS

| | | | |
|---|---|---|---|
| 2007/0010672 A1* | 1/2007 | Yamamoto et al. | 544/333 |
| 2008/0217581 A1* | 9/2008 | Yamamoto et al. | 252/301.16 |
| 2011/0155973 A1* | 6/2011 | Lenz et al. | 252/586 |
| 2012/0161117 A1* | 6/2012 | Chen et al. | 257/40 |

OTHER PUBLICATIONS

Lu et al."Helical Assembly Induced by Hydrogen Bonding from Chiral Carboxylic Acids Based on Perylene Bisimides" J. Phys. Chem. B 2011, 115(37), 10871-10876.*

Huang et al. "Perylene-3,4,9,10-tetracarboxylic Acid Diimides: Synthesis, Physical Properties, and Use in Organic Electronics" J. Org. Chem. 2011, 76, 2386-2407.*

Refiker et al. "Amphiphilic and chiral unsymmetrical perylene dye for solid-state dye-sensitized solar cells" Turk. J. Chem. 2011, 35, 847-859.*

Wurthner, F. "Perylene bisimide dyes as versatile building blocks for functional supramolecular architectures" Chem. Commun. 2004, 1564-1579.*

* cited by examiner

*Primary Examiner* — Joseph Kosack
*Assistant Examiner* — Amanda L Aguirre
(74) *Attorney, Agent, or Firm* — Foley & Lardner LLP

(57) ABSTRACT

A quantitative model that describes the assembly of diketopyrrolopyrrole-based donors and a perylenediimide acceptor into chiral superstructures, as a result of both hydrogen bonding and π•••π stacking. This model provides thermodynamic parameters ($\Delta H°$ and $\Delta S°$) for all noncovalent interactions involved in the assembly and explains the subtle supramolecular cues that convert disordered aggregates into well-defined helical assemblies.

9 Claims, 12 Drawing Sheets

| Molecule | Structure | Thermodynamic and Structural Properties |
|---|---|---|
| 1 dimer | 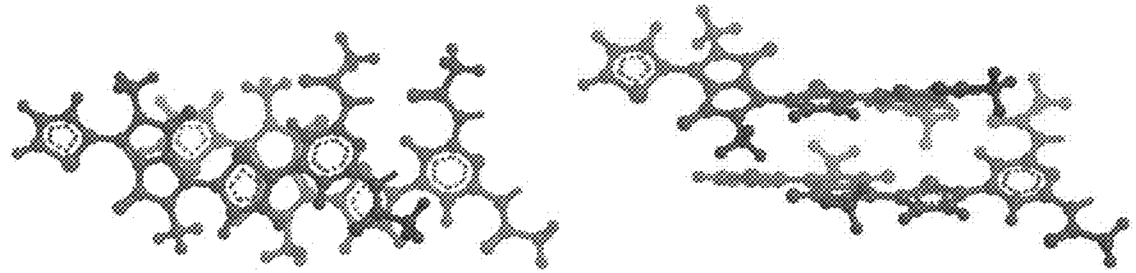 | ΔH = −10.55 kcal/mol |
| H-Bonded 1 and 3 | 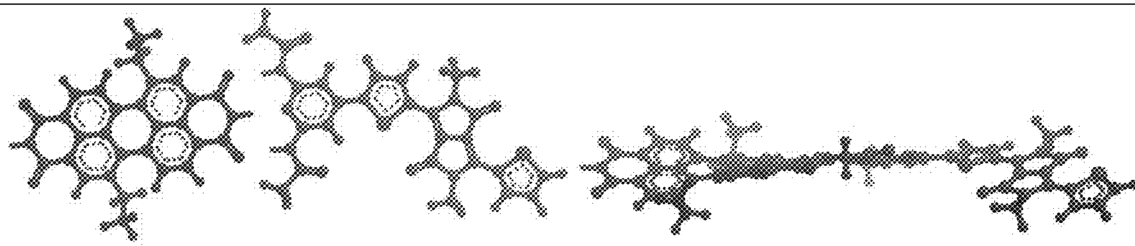 | ΔH = −17.77 kcal/mol |
| 1 and 3 heteroaggregate | 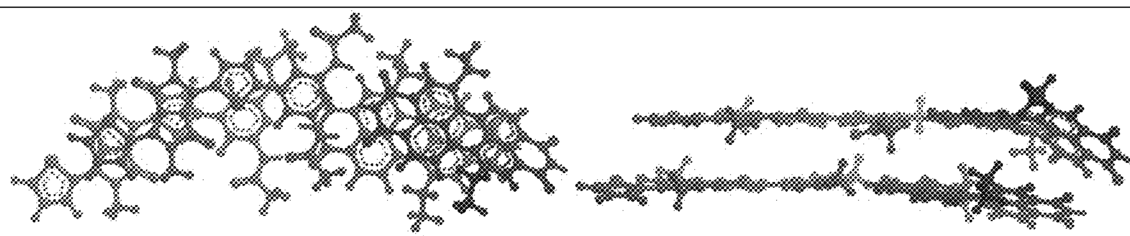 | $\Delta H_\pi$ = −6.34 kcal/mol<br>$\Delta H_H$ = −35.53 kcal/mol<br>$\Delta H_{tot}$ = −41.87 kcal/mol |

SUPERSTRUCTURES OF DIKETOPYRROLOPYRROLE DONORS AND PERYLENEDIIMIDE ACCEPTORS FORMED BY HYDROGEN-BONDING AND π•••π STACKING

CROSS-REFERENCE TO RELATED APPLICATIONS

This application claims priority from U.S. Provisional Application 61/768,973, filed Feb. 25, 2013, and is incorporated herein by reference in its entirety.

STATEMENT OF GOVERNMENT INTEREST

The United States Government has rights in the invention described herein pursuant to an Army Research Office Short Term Innovative Research Award Number W911NF-12-1-0125.

FIELD OF THE INVENTION

The field of the certain embodiments of invention generally relates. More specifically, the field of certain embodiments of invention relates to.

BACKGROUND OF THE INVENTION

Small molecules that self-assemble into well-ordered hierarchical superstructures direct the most complex tasks in biology. To create synthetic structures with similar functionality, chemists have employed noncovalent interactions to organize chromophores into large, well-defined structures, including systems that utilize both hydrogen-bonding (H-bonding) and π•••π interactions. Examples include homoaggregates, such as oligo(p-phenylenevinylenes) (OPVs) or substituted perylenediimides (PDI), where H-bonding precedes aggregation into π-stacked helices, or heteroaggregates that assemble into superstructures via multiple noncovalent interactions, such as a system consisting of either melamine or OPVs H-bonding with PDIs. In self-assembling systems where one-dimensional aggregates form, models have been developed to obtain association constants ($K_a$s), thermodynamic parameters ($\Delta H°$ and $\Delta S°$), and degrees of polymerization by attributing assembly to a single "dominant" noncovalent interaction. For heteroaggregation however, models that consider two or more components are rare and most simplify their description of assembly by only considering a single noncovalent interaction. This inability to model how different noncovalent recognition events work in concert to create superstructures limits the ability of scientists to create systems with the functional complexity found in natural systems.

SUMMARY OF THE INVENTION

One embodiment of the invention relates to a method of assembling heteroaggregates. A first component is interacted with a second component via a first noncovalent interaction to form a substructure. A plurality of substructures are assembled via a second noncovalent interaction to form a superstructure.

One embodiment of the invention relates to a method of assemblying heteroaggregates. A plurality of first components are interacted to form a disordered aggregation. A plurality of second components are interacted with the disordered aggregation. A superstructure is assembled comprising first components hetereoaggregated with second components and first components homoaggregated with first components.

One embodiment of the invention related to a self-assemblying composition. The composition comprises a plurality of diketopyrrole donors and a plurality of perylendiimide acceptors. Each of the plurality of diketopyrrole donors interacts with another of the plurality of diketopyrrole donors via π•••π stacking and noncovalently interacts with one of the plurality of perylendiimide acceptors.

Additional features, advantages, and embodiments of the present disclosure may be set forth from consideration of the following detailed description, drawings, and claims. Moreover, it is to be understood that both the foregoing summary of the present disclosure and the following detailed description are exemplary and intended to provide further explanation without further limiting the scope of the present disclosure claimed.

BRIEF DESCRIPTION OF THE DRAWINGS

The foregoing and other objects, aspects, features, and advantages of the disclosure will become more apparent and better understood by referring to the following description taken in conjunction with the accompanying drawings, in which.

DETAILED DESCRIPTION OF THE PREFERRED EMBODIMENTS

Figures 1A, 1B, 1C:
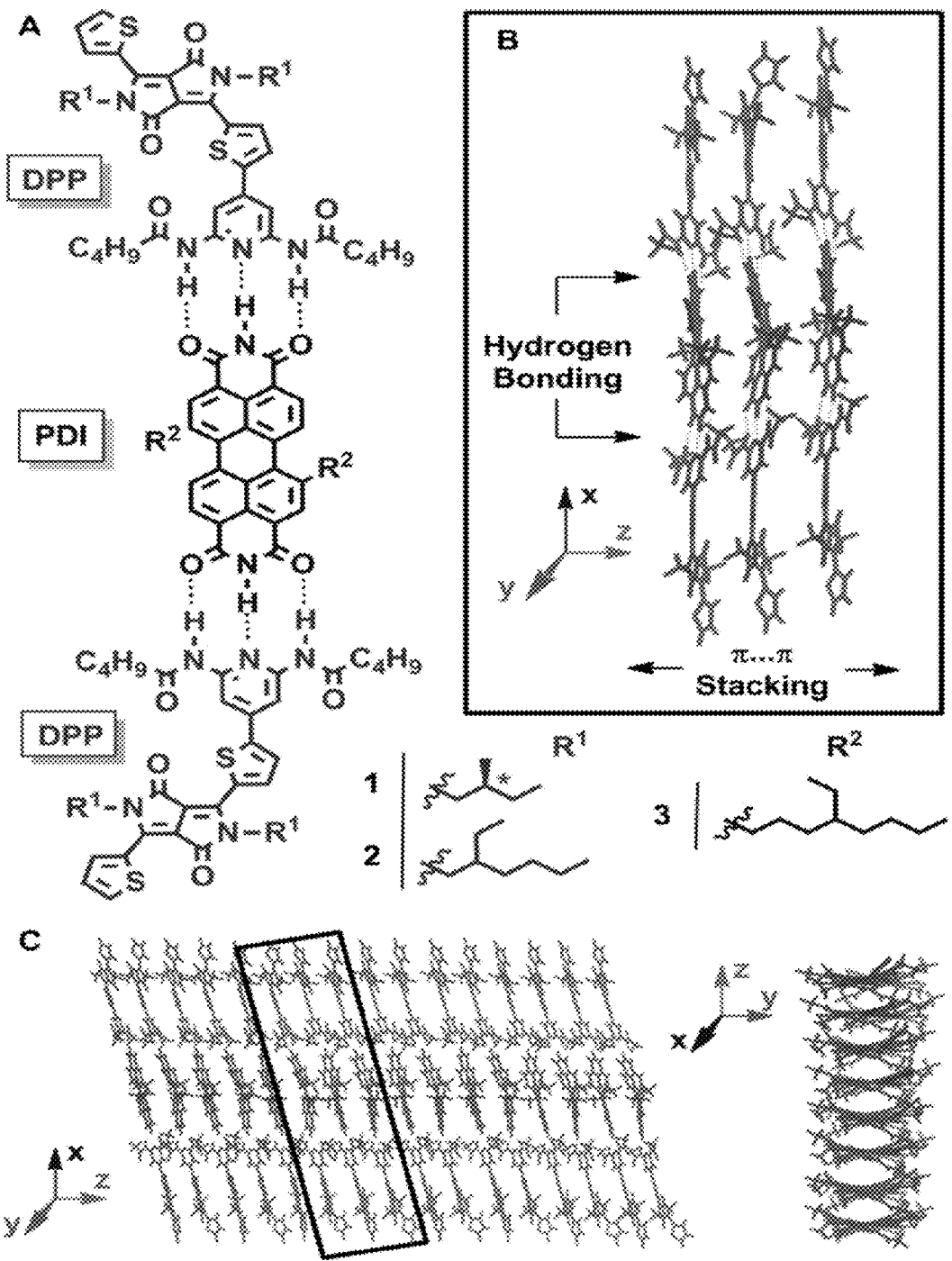
FIGS. 1A-C. A) DPP Donor and PDI acceptor molecules 1-3 are capable of B) heteroaggregation through a combination of H-bonding and π•••π stacking, resulting in C) well-ordered superstructures.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

To develop new, quantitative models that describe how multiple noncovalent interactions bring together different components into well-defined superstructures, the aggregation of chiral and achiral diketopyrrolopyrrole-based (DPP) donors with a 1,7-substituted PDI acceptor (FIG. 1A) were studied. Upon mixing in solution, the PDI and DPPs assemble into well-ordered three dimensional superstructures (FIG. 1C) because of: (1) complementary triple H-bonds along one spatial axis (x), (2) large aromatic surfaces that drive aggregation via π•••π stacking along an orthogonal axis (z), and (3) solubilizing alkyl chains appended to each aromatic core that can interact along the third orthogonal axis (y) (FIG. 1B). Variable temperature (VT) UV/Vis and circular dichroism (CD) spectroscopic measurements revealed that the PDIs associate to disordered DPP aggregates, which subsequently reorganize into helical heteroaggregates of a single chirality. The resulting thermodynamic model quantifies the thermodynamic binding parameters ($\Delta H°$ and $\Delta S°$) associated with each interaction and elucidates the subtle supramolecular cues that induce the transition from disordered aggregates into well-defined helices.

DPP donor 1 and DPP donor 2 have diamidopyridine (DAP) groups, which can form triple H-bonds with the diimide groups of PDI acceptor 3 (FIG. 1a). The donors differ only by their N-alkyl chains: DPP donor 1 possesses homochiral (S)-2-methylbutyl side chains, and 2 has racemic 2-ethyloctyl chains. Initially, the aggregation of DPP donor 1 and PDI acceptor 3 was analyzed by UV/Vis spectroscopy because of the necessity to understand how the propensity to homoaggregate contributes to the formation and structure of heteroaggregates. The UV/Vis spectra of DPP donor 1 in toluene has absorption maxima at 538 and 580 nm at 25° C., which are the result of dipole allowed $S_0$-$S_1$ electronic transitions.

Figures 2A, 2B, 2C, 2D, 2E, 2F:
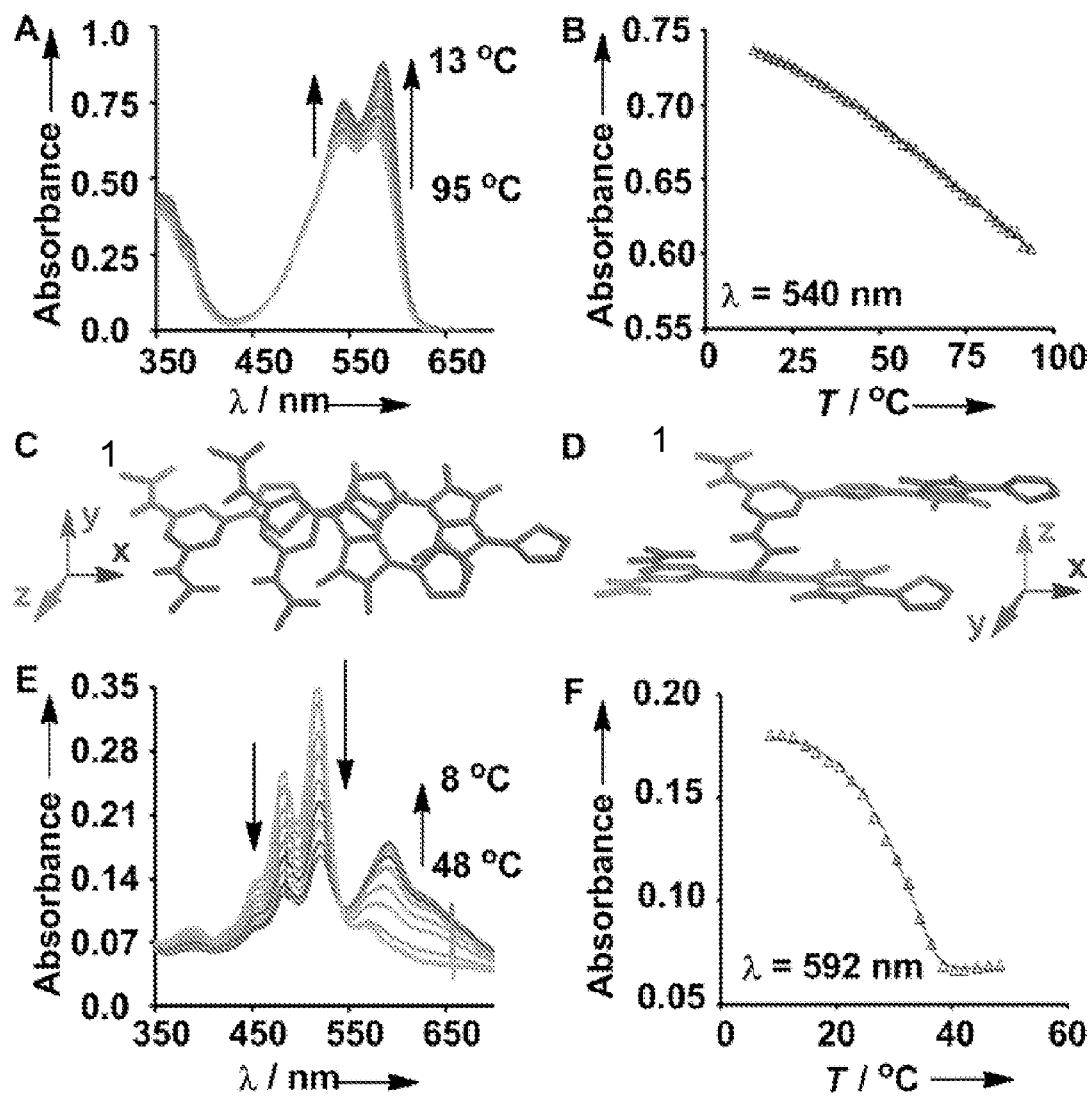
FIGS. 2A-F. A) VT UV/Vis spectra of a 20 µM solution of 1 in toluene. B) The absorbances at 540 nm in the VT UV/Vis for 1 fit to an isodesmic model. C) Top and D) side view of a DFT calculated structure of a π•••π stacked DPP dimer. E) VT UV/Vis spectra of a 35 µM solution of 3 in toluene. F) The absorbance at 592 nm in the VT UV/Vis for 3.

These bands undergo bathochromic shifts with increasing sharpness upon cooling, which are spectral signatures of J-type aggregation (FIG. 2A). Although π-stacked chromophores with chiral side-chains often form chiral superstructures, the absorbance intensities exhibit a sigmoidal dependence with temperature and no observable signal was found in VT CD experiments. These observations indicate isodesmic stacking is occurring, where the binding constant describing the π•••π stacking is constant regardless of aggregate size. By fitting the changes in absorbance to an isodesmic model, $\Delta H°$ and $\Delta S°$ were determined to be $-7.4\pm0.5$ kcal $mol^{-1}$ and $-3.0\pm2.0$ e.u. respectively, indicating the π•••π stacking is enthalpically driven (FIG. 2B). DFT calculations (B3LYP/6-31G(d,p)) on homoaggregates of a DPP that has methyl side chains to simplify the calculation revealed a slip-stacked binding geometry with thiophenes overlapping the diketopyrolopyrolle core (FIGS. 2C and 2D), which has been observed in a previously reported X-ray crystal structure of DPP-thiophene oligomers. The energy of binding ($\Delta E=-10.5$ kcal $mol^{-1}$) from the density functional theory (DFT) calculations agrees well with the $\Delta H°$ derived from the fitting. Interestingly, intermolecular H-bonding between the DAP groups was observed in the calculated structure.

The ability to H-bond is known to affect the supramolecular assembly of 1,7-substituted PDIs, so the homoaggregation of PDI acceptor 3 was also investigated by VT UV/Vis spectroscopy. The UV/Vis spectra of 1,7-substituted PDIs typically display characteristic peaks arising from the $S_0$-$S_1$ transition that are broadened because of twisting in the perylene ring system that inhibits aggregation beyond π-stacked dimers. Previously studied PDIs without N-substituents display a sharp peak that is attributed to the J-aggregation of π•••π stacked dimers interconnected by H-bonding. Alternatively, mono-N-substituted PDIs possessing complementary melamine moieties H-aggregate into helical superstructures as a result of intermolecular H-bonding. For PDI acceptor 3, the UV/Vis spectra revealed a sharp absorbance maximum at 520 nm in toluene with pronounced vibronic fine structure. Upon cooling, these peaks decrease with a concomitant increase of a broad band with a maximum at 592 nm (FIG. 2E). These spectral changes are similar to PDIs whose π•••π aggregation is intermediate between J- or H-type. It is believed that the new absorption peak is attributable to a similar stacking geometry. A plot of the absorbance at 592 nm versus temperature reveals negligible aggregation above 37° C., and below which absorption increases quickly, suggesting nucleation-growth assembly, in which an initial disfavored binding event precludes the formation of long stacks prior to the critical temperature, after which a new thermodynamically favored equilibrium arises that governs the assembly into π-stacked superstructures (FIG. 2F). Suspecting intermolecular H-bonding plays a key role in assembly, the VT UV/Vis experiment was repeated with a bis-N-cyclohexyl derivative of PDI acceptor 3 or in 3% DMSO in toluene, both of which inhibit H-bonding. No spectral changes that indicate π-stacking were observed in either control experiment, confirming that H-bonding promotes the π-stacking of PDI acceptor 3.

Figures 3A, 3B, 3C, 3D:
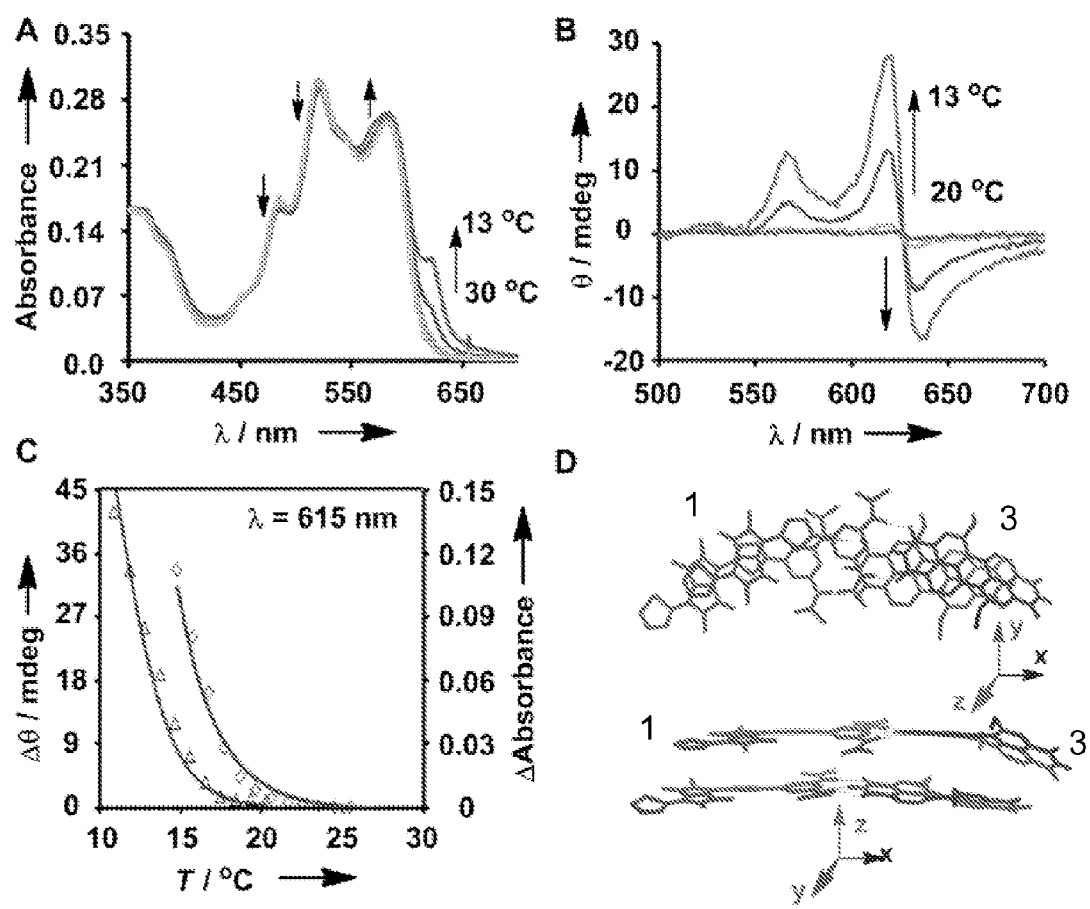
FIGS. 3A-D. A) VT UV/Vis and B) Circular Dichroism (CD) spectra of a 70 µM solution of 1 in toluene with 0.5 molar equivalents of 3. C) The absorbance (◇) and elipticity (Δ) at 615 nm obtained by VT UV/Vis and CD respectively fit to a cooperative helix formation model. D) Top and side view of a DFT calculated structure of two 1:3 H-bonded dimers π•••π stacked.

Heteroaggregate formation was investigated by VT UV/Vis spectroscopy on a 2:1 mixture of DPP donor 1 and PDI acceptor 3, respectively, in toluene. At 40° C., the spectrum is a linear composite of the individual spectra (FIG. 3A), indicating that mixed π-aggregates are not present at high temperature. Upon cooling, the absorbance bands corresponding to PDI acceptor 3 decrease and two new bands arise at 563 and 615 nm, which are assigned to a $S_o$-$S_1$ transition from the π•••π stacking of PDI acceptor 3. Several aspects of the spectrum indicate heteroaggregate formation: 1) the absorbance at 615 nm begins to increase in the mixture at 21° C., which is a much lower temperature than was observed for the onset of homoaggregates of PDI acceptor 3 (39° C.), 2) the new bands at 563 and 615 nm are much sharper than the broad peaks formed by homoaggregates of PDI acceptor 3, suggesting J-type aggregation, meaning the π-stacked PDIs adopt a different geometry in the heteroaggregates, and 3) the change in the absorption at 615 nm for the mixture of DPP donor 1 and PDI acceptor 3 is more gradual (FIG. 3C) than for the homoaggregates of PDI acceptor 3, suggesting that homoaggregation pathways are suppressed and a different assembly mechanism is operating that is driven by the triple H-bonding between DPP donor 1 and PDI acceptor 3. Prior to the appearance of the PDI π-stacking bands 563 and 615 nm, the transitions previously assigned to π-stacking of DPP donor 1 (538 and 580 nm) increase steadily with decreasing temperature, suggesting extensive homoaggregation of DPP donor 1 precedes heteroaggregate formation. A bisignated Cotton effect, with peaks at 563 and 615 nm matching the π-stacking peaks of the achiral PDI, appeared in the VT CD spectra. The bisignated effect is a consequence of electronic coupling between conjugated segments in a helical array (FIG. 3B). Notably, the transition temperature in the VT CD spectrum of the heteroaggregates is 5° lower than in the UV/Vis measurements, suggesting several molecules of PDI acceptor 3 need to be associated onto disordered aggregates of DPP donor 1 to induce rearrangement into chiral helices (FIG. 3C).

The VT UV/Vis experiments were repeated in a mixture of DPP donor 2 and PDI acceptor 3 (FIG. 11), and while the same trends were observed in the VT UV/Vis spectra, no Cotton effect arose in the CD spectrum of DPP donor 2 and PDI acceptor 3. The structure of the heteroaggregate of DPP donor 1 and PDI acceptor 3 was modeled by DFT calculations using methyl and ethyl solubilizing chains on DPP and PDI, respectively. The π•••π overlap between the DPPs remains almost unchanged compared to DPP homoaggregates whereas the PDI relative orientations did change compared to PDI homoaggregates, indicating that the preferred conformation of the DPPs dictates the π•••π stacking angle in the heteroaggregate superstructure. Furthermore, the assessment of PDI J-aggregation from the VT UV/Vis spectrum of the heteroaggregate is supported by the skewed orientation of the PDIs in the calculated structure (FIG. 3D).

Figure 4:
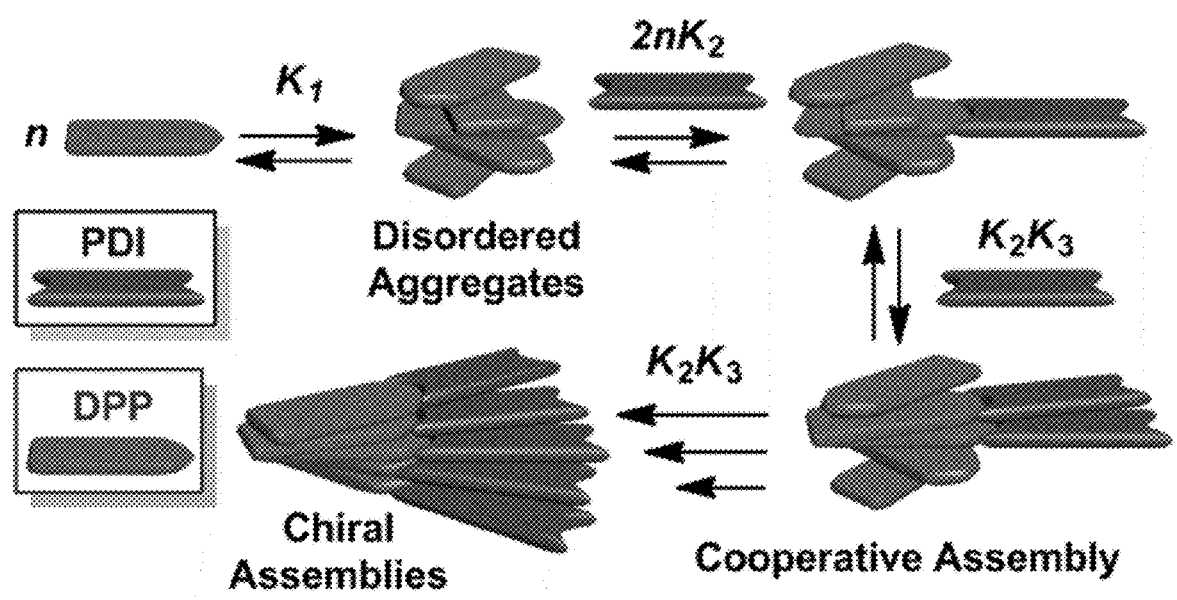
FIG. 4. The proposed model for the heteroaggregation of the DPPs and PDIs into chiral assemblies.

The spectroscopic data were used to derive a new assembly model that describes formation of heteroaggregates that arise from both H-bonding and π•••π stacking. The corresponding thermodynamic parameters for each interaction were obtained by fitting to the changes in absorption with temperature to this model. The data indicate that PDIs bind to disordered stacks of DPPs to produce chiral superstructures (FIG. 4), which leaves an available H-bonding site on each PDI that can potentially be occupied by an additional DPP at higher concentrations. In the model (FIG. 4), disordered homoaggregates of DPP donor 1 assemble isodesmically according to microscopic binding constant $K_1$. Since there are four identical pathways by which this process can occur, $K_1$ is one-fourth the experimentally observed macroscopic $K_a$. The initial association event of one molecule of PDI acceptor 3 to a stack of DPP donor 1 of any size is governed by microscopic association constant $K_2$ (FIG. 4B). As there are two positions where H-bonding takes place in PDI acceptor 3 and n points on a stack of DPP donor 1, where n denotes the number of residues, the macroscopic $K_a$ is $2nK_2$. Further association of PDI acceptor 3 to the stacks are described by $K_2$ and $K_3$, where $K_3$ is a dimensionless $K_a$ that includes the energy contributions from π•••π stacking and any chelate cooperativity effects (FIG. 4) associated with the aggregation of PDI acceptor 3 within the DPP donor 1 stacks. The resulting mass balance equations can be written as an infinite series that describes the total concentration of each species, $[PDI]_t$ and $[DPP]_t$, as a function of n:

$$[DPP]_t = [DPP] \tag{1}$$

$$\sum_{n=1}^{\infty} \left( (n(4K_1[DPP])^{n-1}) \left( 1 + 2nK_2[PDI] \sum_{i=0}^{n-1} (K_2K_3[PDI])^i \right) \right)$$

$$[PDI]_t = [PDI] + 2K_2[PDI][DPP] \tag{2}$$

$$\sum_{n=1}^{\infty} \left( (n(4K_1[DPP])^{n-1}) \left( \sum_{i=0}^{n-1} ((i+1)(K_2K_3[PDI])^i) \right) \right)$$

Equations 1 and 2 are both convergent and can be solved to obtain [PDI] and [DPP] for any value of $K_1$, $K_2$, $K_3$, $[PDI]_t$, and $[DPP]_t$. $\Delta H°$ and $\Delta S°$ corresponding to $K_1$ were fixed to the values previously obtained by studying the homoaggregation of DPP donor 1 and held invariant. By generating K values from the van't Hoff equation, the concentration of all species at each temperature can be obtained by fitting the experimental VT data. When both VT UV/Vis and CD measurements were simultaneously fit to the same parameter set, the $\Delta H°$ and $\Delta S°$ for $K_2$ ($-24.1\pm0.1$ kcal mol$^{-1}$ and $-70\pm2$ e.u.) and $K_3$ ($-13.5\pm0.1$ kcal mol$^{-1}$ and $-40\pm1$ e.u.) were obtained. These values indicate $K_2$ is enthalpically driven, which is typical for H-bonded dimers. Interestingly, $K_3$ is also enthalpically driven, but an entropic penalty is associated with the rearrangement of PDI acceptor 3 into J-aggregates, presumably because the contorted perylene rings disfavor this stacking geometry. Nevertheless, the enthalpy associated with π-aggregation overcomes the disfavorable entropy below room temperature, which drives heterosuperstructure formation upon cooling.

In one embodiment, the self-assembly of heteroaggregates comprised of α-conjugated donors and acceptors provides synthetic hierarchical structures with functional complexity comparable to their biological counterparts, but models are needed that can describe the complex milieu of interactions involved in superstructure formation. By studying the heteroaggregation of a DPP donor and PDI acceptor a new model was elucidates the subtle structural cues that induce the transition from a disordered aggregate into a chiral helix. Using this new model, all thermodynamic parameters could be quantitatively determined, and both H-bonding and the subsequent helix formation process were found to be enthalpically favored but entropically disfavored. This new model could be used to create ordered superstructures of donors and acceptors, which are increasingly investigated in the context of photovoltaics and for understanding fundamental aspects of charge and energy transport in self-assembled systems.

EXAMPLES

1. General Methods

All solvents were dried using a Pure Solv MD-6 solvent purification system. All reagents and starting materials were purchased from commercial sources and used without further purification unless otherwise noted. Aqueous solutions were prepared from nanopure water purified from a Milli-Q plus system (Millipore Co.), with a resistivity over 18 MΩ cm$^{-1}$. Chromatography purifications were performed using Sorbent Technologies Silica Gel (60 Å, 65×250 mesh). Thin-layer chromatography (TLC) was carried out using aluminum sheets precoated with silica gel 60 (EMD 40-60 mm, 230-400 mesh with 254 nm dye). TLC plates were visualized by UV-light and stained using a p-anisaldehyde or phosphomolybdic acid solution if required. All reactions were carried out under an inert atmosphere of $N_2$ using standard Schlenk techniques unless otherwise noted. NMR spectra were obtained on either a Bruker AVANCE 400 or 500 MHz spectrometers. All chemical shifts are reported in δ units using the solvent residual signal as an internal standard and the coupling constant values (J) are reported in Hertz (Hz). The following abbreviations are used for signal multiplicities: s, singlet; d, doublet; t, triplet; q, quartet; quintet (qui); sextet (sex); m, multiplet; and br, broad. Electrospray Ionization Mass Spectroscopy (ESI-MS) spectra were acquired on an Agilent LC/MSD Trap XCT system. High-resolution mass spectral analyses were carried out on an Agilent 6200 LC/MSD TOF System. UV/Vis measurements were performed on an Agilent 8453 spectrophotometer equipped with a temperature control accessory. Circular Dichroism (CD) measurements were performed on an Aviv Circular Dichroism Spectrometer Model 215. For all UV/Vis and CD measurements, the temperatures were corrected using an external digital thermometer with a microprobe accessory.

2. Synthesis

Figure 5:
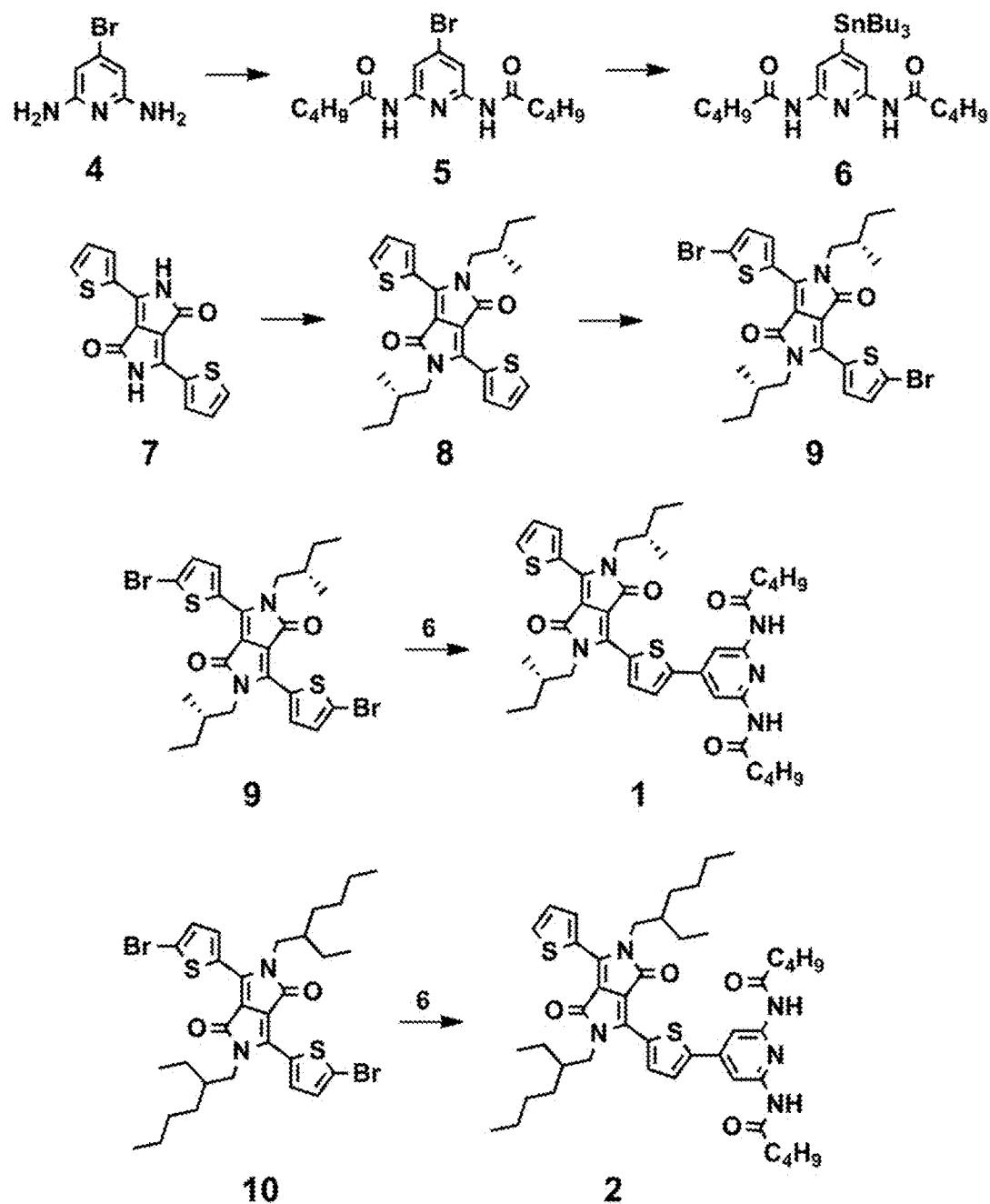
FIG. 5. Preparation of DPP donor 1 and DPP donor 2.
Figure 6:
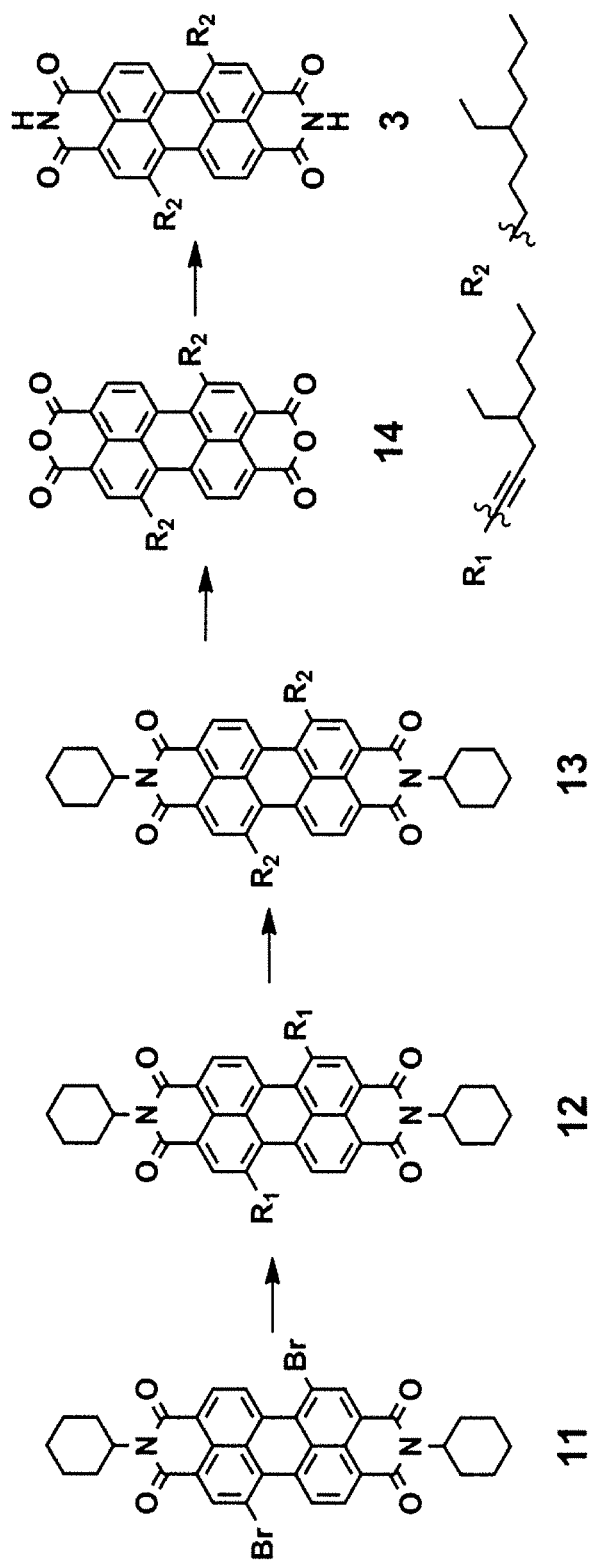
FIG. 6. Preparation of PDI acceptor 3.

FIG. 5 illustrates the synthesis of DPP Donor 1 and DPP Donor 2. 4-Bromo-2,6-diaminopyridine, compound 4, was prepared following a previously reported synthetic protocol. Di-bromo-di-alkyl-DPP, compound 10 was prepared following the method described by Yang and co-workers.

4-Bromo-2,6-divalerylamidopyridine (compound 5): compound 4 (0.93 g, 4.95 mmol) and Et$_3$N (2.1 mL, 14.85 mmol) were dissolved in CH$_2$Cl$_2$ (50 mL). To this mixture a solution of valeryl chloride (1.75 mL, 14.85 mmol) in CH$_2$Cl$_2$ (1.5 mL) was added dropwise. Progress of the reaction was monitored by TLC. Upon completion (1.5 hr) the reaction mixture was washed with saturated NaHCO$_3$ solution (aq, 30 mL), HCl (aq, 0.1 M, 30 mL) and brine (30 mL). The remaining organic portion was dried over MgSO$_4$, and concentrated under reduced pressure. The residue was further purified by column chromatography (SiO$_2$, 3:1 hexanes:EtOAc) to afford compound DPP donor 1 as off-white crystals (1.7 g, 97%) with identical characterization data to that previously reported in the literature.

2,6-Divalerylamido-4-tributylstannylpyridine (compound 6): compound 5 (1.03 g, 2.88 mmol), bis(tributyltin) (8.36 g, 14.4 mmol) and dichloropalladium(bistriphenylphosphine) (40 mg, 0.058 mmol) were refluxed in toluene (30 mL) for 3 h. After cooling to room temperature, the reaction mixture was added to a column of silica gel. Elution first with hexanes removed unreacted bis(tributyltin), further elution with 5:1 hexanes:EtOAc resulted the desired compound 2 as beige crystals (1.0 g, 61%). $^1$H NMR (400 MHz, CDCl$_3$, 25° C.): δ 8.02 (s, 2H), 7.59 (s, 2H), 2.34 (t, J=8.0 Hz, 4H), 1.68 (qui, J=8 Hz, 4H), 1.52 (qui, J=8 Hz, 6H), 1.38 (sex, J=8 Hz, 4H), 1.30 (sex, J=8 Hz, 6H), 1.09 (t, J=8.0 Hz, 4H), 0.92 (t, J=8.0 Hz, 6H), 0.86 (t, J=8.0 Hz, 9H) ppm. $^{13}$C NMR (400 MHz, CDCl$_3$, 25° C.): δ 171.45, 159.93, 148.10, 116.66, 37.49, 28.89, 27.37, 27.21, 22.30, 13.75, 13.61, 9.69 ppm. HRMS m/z calculated for C$_{27}$H$_{49}$N$_3$O$_2$Sn [(M+H)$^+$] 568.2925, found 568.2901.

N,N'-(4-(5-(2,5-bis(2-ethylhexyl)-3,6-dioxo-4-(thiophen-2-yl)-2,3,5,6-tetrahydropyrrolo[3,4-c]pyrrol-1-yl)thiophen-2-yl)pyridine-2,6-diyl)dipentanamide (DPP donor 2): compound 10 (0.19 g, 0.28 mmol), compound 6 (0.35 g, 0.61 mmol) and dichloropalladium(bistriphenylphosphine) (19 mg, 0.028 mmol) were dissolved in toluene (10 mL) and stirred under reflux overnight. The reaction mixture was concentrated under reduced pressure, and the residue was purified by column chromatography (SiO$_2$ 5:1 CH$_2$Cl$_2$:EtOAc) to provide DPP donor 1 as purple crystals (0.1 g, 45%). $^1$NMR (400 MHz, CDCl$_3$, 25° C.): δ 8.92 (dd, J=1.2, 4.0 Hz, 1H), 8.90 (d, J=4.0 Hz, 1H), 8.25 (s, 2H), 7.66 (d, J=4.0 Hz, 1H), 7.64 (dd, J=1.2, 4.0 Hz, 1H), 7.63 (s, 2H), 7.27 (d, J=4.0 Hz, 1H), 4.08-4.02 (m, 4H), 2.40 (t, J=8 Hz, 4H), 1.87 (b, 2H), 1.72 (qui, J=8 Hz, 4H), 1.47-1.23 (m, 21H), 0.96 (t, J=8 Hz, 6H), 0.92-0.82 (m, 12H) ppm. $^{13}$C NMR (400 MHz, CDCl$_3$, 25° C.): δ 171.62, 161.72, 161.66, 150.23, 146.17, 144.80, 140.85, 139.65, 136.34, 135.59, 130.80, 130.78, 129.76, 128.47, 127.01, 108.83, 108.11, 105.75, 77.32, 77.01, 76.69, 45.93, 39.30, 39.07, 37.54, 30.32, 30.22, 28.43, 28.35, 27.32, 23.65, 23.55, 23.06, 22.31, 14.01, 13.97, 13.79, 10.56, 10.51 ppm. HRMS m/z calculated for C$_{45}$H$_{61}$N$_5$O$_4$S$_2$ [(M+H)$^+$] 800.4243, found 800.4223.

2,5-Dimethylbutyl-3,6-dithiophen-2-ylpyrrolo[3,4-c]pyrrole-1,4-dione (compound 8). Compound 7 (5.00 g, 16.7 mmol) and anhydrous K$_2$CO$_3$ (9.23 g, 66.9 mmol) were dissolved into DMF (100 mL) and heated to 120° C. under N$_2$. (S)-(+)-1-Iodo-2-methylbutane (14.8 g, 74.7 mmol) was added and the mixture was stirred for 15 h at 125° C. The solution was cooled to room temperature, poured into 1 L of ice water, filtered, and the filter cake was washed thoroughly with H$_2$O and MeOH. After drying in vacuo, the crude product was purified by column chromatography (SiO$_2$, CH$_2$Cl$_2$) to provide 8 as a dark red powder (2.20 g, 30%) $^1$H NMR (400 MHz, CDCl$_3$, 25° C.): 8.97 (dd, J=1.2, 4.0 Hz, 2H), 7.63 (dd, J=1.2, 4.0 Hz, 2H), 7.27 (dd, J=4.0, 5.2 Hz, 2H), 4.04-3.93 (m, 4H), 1.88-1.96 (m, 2H), 1.53-1.45 (m, 2H), 1.28-1.21 (m, 2H), 0.93-0.89 (m, 12H) ppm. $^{13}$C NMR (400 MHz, CDCl$_3$, 25° C.): 161.73, 140.35, 135.53, 130.62, 129.90, 128.49, 107.80, 47.61, 35.43, 26.98, 16.60, 11.27. HRMS m/z calculated for C$_{24}$H$_{29}$N$_2$O$_2$S$_2$ [(M+H)$^+$]: 440.15922, found 440.157611.

2,5-Dimethylbutyl-3,6-bis(5-bromothiophen-2-yl)pyrrolo[3,4-c]-pyrrole-1,4-dione (compound 9). Compound 8 (5.03 g, 11.4 mmol) and N-bromosuccinimide (4.17 g, 23.4 mmol) were dissolved in CHCl$_3$ (300 mL) and stirred at rt for 20 h. The mixture was poured into 300 mL of MeOH, and the precipitate was collected by vacuum filtration. The filter cake was thoroughly washed with MeOH and dried in vacuo to provide 9 as a dark solid (4.43 g, 65%). $^1$H NMR (400 MHz, CDCl$_3$, 25° C.): 8.71 (s, 2H), 7.23 (dd, J=4.0 Hz, 2H), 3.95-3.83 (m, 4H), 1.93-1.85 (m, 2H), 1.50-1.45 (m, 2H), 1.28-1.17 (m, 2H), 0.94-0.90 (m, 12H) ppm. $^{13}$C NMR (400 MHz, CDCl$_3$, 25° C.): 161.38, 139.35, 135.63, 131.54, 131.20, 119.14, 107.89, 47.72, 35.45, 26.92, 16.59, 11.22 HRMS m/z calculated for C$_{24}$H$_{27}$Br$_2$N$_2$O$_2$S$_2$ [(M+H)$^+$]: 596.9881, found 596.9856.

N,N'-(4-(5-(2,5-bis((S)-2-methylbutyl)-3,6-dioxo-4-(thiophen-2-yl)-2,3,5,6-tetrahydropyrrolo[3,4-c]pyrrol-1-yl)thiophen-2-yl)pyridine-2,6-diyl)dipentanamide (DPP Donor 1). compound 9 (1.25 g, 2.1 mmol), 6 (0.6 mg, 1.1 mmol) and dichloropalladium(bistriphenylphosphine) (34 mg, 0.05 mmol) were dissolved in toluene (10 mL) and stirred under reflux overnight. After cooling to rt, the reaction mixture was concentrated in vacuo and the residue was purified by column chromatography (SiO$_2$, 5:1 CH$_2$Cl$_2$:EtOAc) to provide DPP donor 2 as purple crystals (0.3 g, 20%). $^1$H NMR (400 MHz, CDCl$_3$, 25° C.): 9.01 (d, J=4.0 Hz, 1H), 8.93 (d, J=4.0 Hz, 1H), 8.22 (s, 2H), 7.70 (bs, 2H), 7.67 (d, J=4.0 Hz, 1H), 7.64 (dd, J=1.2, 4.0 Hz, 1H), 7.27 (d, J=4.0 Hz, 1H), 4.07-3.93 (m, 4H), 2.42 (t, J=8 Hz, 4H), 1.92 (m, 2H), 1.73 (qui, J=8 Hz, 4H), 1.53-1.47 (m, 2H), 1.42 (sex, J=8 Hz, 4H), 1.27-1.19 (m, 2H), 0.98-0.89 (m, 18H) ppm. $^{13}$C NMR (500 MHz, CDCl$_3$, 25° C.): δ 171.88, 161.71, 161.62, 150.16, 146.13, 144.91, 140.87, 139.49, 136.45, 135.94, 130.99, 129.82, 128.58, 127.19, 108.82, 107.99, 105.72, 47.67, 37.60, 35.58, 35.42, 27.37, 27.02, 26.98, 22.35, 16.74, 16.61, 13.83, 11.29 ppm. HRMS m/z calculated for C$_{39}$H$_{50}$N$_5$O$_4$S$_2$ [(M+H)$^+$]: 716.3304, found 716.3285.

Synthesis of PDI Molecule 3

N,N'-dicyclohexyl-1,7-Di(4-ethyloctynyl)perylene-3,4:9,10-tetracarboxylic acid diimide (compound 12): Compound 11 (0.878 g, 1.23 mmol) was dissolved in a mixture of toluene (40 mL) and Et$_3$N (20 mL). Then 4-ethyl-1-octyne (0.376 g, 2.72 mmol), dichloropalladium(bistriphenylphosphine) (0.043 g, 0.06 mmol), and CuI (0.023 g, 0.12 mmol) were added successively, and the resulting reaction mixture was heated under reflux for 12 h. After cooling to rt and concentrating under reduced pressure, the residue was redissolved in CH$_2$Cl$_2$ (50 mL) and washed with H$_2$O (150 mL). The organic layer was then dried over MgSO$_4$ and concentrated. The residue was purified by column chromatography (SiO$_2$ 1:2 CH$_2$Cl$_2$:hexanes) to afford the desired product as dark-purple solid (0.41 g, 40%). $^1$H NMR (400 MHz, CDCl$_3$, 25° C.): δ 10.08 (d, J=8.0 Hz, 2H), 8.69 (s, 2H), 8.56 (d, J=8.0 Hz, 2H), 5.04 (t, J=12.0 Hz, 2H), 2.66 (t, J=8.0 Hz, 4H), 2.62-2.53 (m, 4H), 1.94-1.91 (m, 4H), 1.80-1.25 (m, 30H), 1.02 (t, J=8.0 Hz, 6H), 0.93 (t, J=8.0 Hz, 6H). $^{13}$C NMR (400 MHz, CDCl$_3$, 25° C.): δ 163.35, 163.11, 137.89, 133.41, 132.84, 129.67, 126.94, 126.81, 126.30, 123.04, 122.07, 120.46, 100.86, 83.16, 53.99, 38.75, 33.18, 29.16, 29.07, 26.59, 26.36, 25.49, 24.11, 22.95, 14.15, 11.22. MALDI-TOF: calculated 827.06, Found: 826.47.

N,N'-dicyclohexyl-1,7-Di(4-ethyloctyl) perylene-3, 4:9,10-tetracarboxylic acid diimide (compound 13): Compound 12 (0.8 g, 0.97 mmol) and 5% Pd/C catalyst (0.4 g) were added to degassed anhydrous THF (200 mL). The reaction mixture was stirred and exposed to a H$_2$ atmosphere for 48 h at rt. The crude solution was filtered and concentrated. The residue was purified by column chromatography (SiO$_2$ 1:3 CH$_2$Cl$_2$:hexanes) to provide compound 13 as orange crystals (0.36 g, 45%). $^1$H NMR (400 MHz, CDCl$_3$, 25° C.): 8.67 (s, 2H), 8.60 (d, J=8.0 Hz, 2H), 8.21 (d, J=8.0 Hz, 2H), 5.10-5.02 (m, 2H), 3.28 (t, J=8.0 Hz, 4H), 2.64-2.54 (m, 4H), 1.94-1.91 (m, 8H), 1.79-1.73 (m, 6H), 1.50-1.25 (m, 28H), 0.89-0.84 (m, 12H). $^{13}$C NMR (400 MHz, CDCl$_3$, 25° C.): δ 164.17, 164.13, 141.18, 134.28, 134.18, 133.14, 129.05, 128.50, 127.98, 126.64, 122.45, 122.36, 53.92, 38.69, 36.27, 33.18, 32.82, 29.17, 28.97, 28.32, 26.56, 25.84, 25.47, 23.09, 14.15, 10.87. HRMS m/z calculated for C$_{56}$H$_{70}$N$_2$O$_4$ [(M+H)$^+$] 835.5414, found 835.5416.

1,7-Di(4-ethyloctyl) perylene-3, 4:9,10-tetracarboxylic acid diimide (compound 3) Compound 13 (0.56 g, 0.67 mmol) and KOH (5.6 g, 0.1 mol) were dissolved in a mixture of t-BuOH (68 mL) and H$_2$O (3.3 mL). The solution was stirred for 25 h under reflux. Subsequently, HCl solution (2 N, 62 mL) was added dropwise to the cooled reaction, and the suspension was stirred for another 6 h. The precipitate (compound 14) was collected by filtration, washed with H$_2$O (100 mL) and air-dried. Without further purification and characterization, compound 14 was combined with NH$_4$OAc (12 g) and dissolved in AcOH (90 mL). The reaction mixture was stirred at 120° C. for 15 h. After cooling to rt, the resulting suspension was diluted with H$_2$O (150 mL). After standing for 1 h, the dark precipitate was collected by filtration, washed with H$_2$O (1 L), and air-dried by aspiration. Further recrystallization in THF afforded compound 3 as a purple black solid (0.30 g, 73%). $^1$H NMR (400 MHz, CDCl$_3$, 25° C.) δ: 8.72 (s, 2H), 8.65 (d, 2H), 8.46 (br, 2H), 8.27 (d, 2H), 3.31 (m, 4H), 1.97 (m, 4H), 0.83-1.42 (m, 22H), 0.85 (m, 12H). HRMS: m/z calculated for C$_{44}$H$_{50}$N$_2$O$_4$ [(M+H)$^+$]: 671.3843, Found: 671.3846.

3. Aggregation Models

General

Changes in the UV/Vis or CD spectra of DPPs, PDIs, or mixtures thereof were induced by changes in the sample temperature or concentration. This is the result of the formation or disassembly of aggregates of varying size composed of DPPs and/or PDIs in differing local environments with differing propensity to absorb light at various wavelengths. Accordingly, equilibrium constants, $K_a$s, can be quantified by first defining a model that includes the appropriate set of equilibria, calculating the hypothetical concentrations of equilibrium species at each temperature or concentration, and finally fitting the resulting data to the spectra and their changes. Fittings were conducted in Microsoft Excel 2010 using the Evolutionary Solving method within the Solver feature by minimizing the total sum of squared residuals (SSR, Equation 1), where w, are the weights assigned to each absorbance.

$$SSR = \sum_i w_i (A_i^{exp} - A_i^{calc})^2 \quad (3)$$

When appropriate, two or more experiments (e.g. variable temperature UV/Vis and CD) are fitted simultaneously to the same enthalpy/entropy parameters to minimize the resulting error.

Aggregation of DPP Donor 1 (Isodesmic Model)

To model the homoaggregation of DPP donor 1, a two-state system was assumed, where the fully monomeric DPP donor 1 and fully aggregated DPP donor 1 each have a unique temperature independent extinction coefficient. The observed absorbance changes in a variable temperature UV/Vis experiment was found to fit well to the simplest infinite association model, the isodesmic model, which assumes the association by π•••π stacking between aromatic moieties are equivalent regardless of length of the stack:

$$K = \frac{[(DPP)_{n+1}]}{[(DPP)_n][DPP]} \quad (4)$$

A commonly overlooked aspect is that the value of $K_a$ derived from the fitting process is typically a macroscopic $K_a$ that does not take into account that there are two faces to which each DPP donor 1 molecule can associate. While a technicality in terms of reporting $K_a$s within the literature, it is of crucial importance when comparing the experimentally derived thermodynamic parameters to those obtained by computational chemistry, which describe the microscopic association process. Since there are a total of four identical pathways by which two DPP molecules can associate, the microscopic association constant, $K_1$, can be defined as:

$$K = 4K_1 = \frac{[(DPP)_{n+1}]}{[(DPP)_n][DPP]} \quad (5)$$

$$[DPP]_t = [DPP] + [(DPP)_2] + [(DPP)_3] + [(DPP)_4] + \ldots \quad (6)$$

Equations 5 and 6 can be combined to give:

$$[DPP]_t = [DPP] + 2(4K_1)[DPP]^2 + 3(4K_1)^2[DPP]^3 + 4(4K_1)^3[DPP]^4 + \ldots \quad (7)$$

Equation 7 can be re-expressed as an infinite series to give:

$$[DPP]_t = [DPP] \sum_{n=1}^{\infty} n(4K_1[DPP])^{n-1} \quad (8)$$

Given the general solution for this infinite series in equation 9, equation 8 can be re-written as equation 8:

$$\sum_{n=1}^{\infty} nx^{n-1} = \frac{1}{(1-x)^2} \quad (9)$$

$$[DPD]_t = \frac{[DPP]}{(1 - 4K_1[DPP])^2} \quad (10)$$

Solving for [DPP] gives equation 11:

$$[DPP] = \frac{8K_3[DPP]_t + 1 - \sqrt{16K_1[DPP]_t + 1}}{32K_1^2[DPP]_t} \quad (11)$$

To fit the variable temperature UV/Vis spectrum, $K_a$s are generated from the van't Hoff equation (Equation 12) and are then used to calculate the hypothetical absorbance at each temperature (Equation 13). The theoretical data is then fit to the experimental spectroscopic data by minimizing the SSR (Equation 3) using the thermodynamic parameters ($\Delta H°$ and $\Delta S°$) and the extinction coefficients as fitting parameters.

$$K = e^{-\frac{\Delta H^0}{RT} + \frac{\Delta S^0}{R}} \quad (12)$$

$$A = ([DPP]_t - [DPP])\varepsilon_{aggregate} + [DPP]\varepsilon_{monomer} \quad (13)$$

Assembly of DPP Donor 1 and PDI Acceptor 3 into Heteroaggregates

Because the ratio of 1:3 in solution (2:1) and the higher number of H-bonds resulting from complementary imides and diamidopyridines, it was assumed that homoaggregation of PDI acceptor 3 does not occur to an appreciable extent under the experimental conditions and is thus not included in our model. Since strong homoaggregation of PDI acceptor 3 occurs without a resulting signal in the CD spectra, the model presumes the DPP donor 1 molecules are present in a broad distribution of chain lengths as a result of isodesmic stacking as dictated by a macroscopic $K_a$ ($4K_1$) determined previously. The binding of PDI Acceptor 3 to each of these stacks can be described by two $K_a$s, $K_2$ and $K_3$. The former describes the strength of association of one 3 molecule to a DPP donor 1 stack of any length that does not already contain PDI acceptor 3. As there are two points by which H-bonding takes place in PDI acceptor 3 and n points on a stack of DPP donor 1 (where n denotes the number of residues), the macroscopic $K_a$ describing this event is $2nK_2$. $K_3$ describes binding strength of additional PDI acceptor 3 molecules to DPP donor 1 stacks already containing PDI acceptor 3 molecules and includes 1) the additional binding energy yielded as a result of $\pi \cdots \pi$ stacking between two PDI moieties and 2) the benefit of chelate cooperativity. For the variable temperature experiments of DPP donor 1 and PDI acceptor 3 (FIGS. 3A and 3B), precipitation of heteroaggregates occurred below 10° C., which prevented the assessment of any new bands at low temperatures.

$$K = 4K_1 = \frac{[(DPP)_{n+1}]}{[(DPP)_n][DPP]} \quad (14)$$

$$2nK_2 = \frac{[(DPP)_n(PDI)]}{[(DPP)_n][(PDI)]} \quad (15)$$

$$K_2K_3 = \frac{[(DPP)_n(PDI)_m]}{[(DPP)_n(PDI)_{m-1}][(PDI)]} \quad n \geq m \quad (16)$$

The components included in the mass balance equation that defines the total concentration of DPP ($[DPP]_t$) for this particular system consist of a series of equations defined by the length of the DPP chain, n:

For$[DPP]_t$:
$n = 1$   $[DPP] + [(DPP)(PDI)]$
$n = 2$   $2[DPP_2] + 2[(DPP)_2(PDI)] + 2[(DPP)_2(PDI)_2]$
$n = 3$   $3[(DPP)_3] + 3[(DPP)_3(PDI)] + 3[(DPP)_3(PDI)_2] + 3[(DPP)_3(PDI)_3]$
$\downarrow$
$n = \infty$ Substituting in equations 14-16 give:

For$[DPP]_t$:

$n = 1$   $[DPP] + (2K_2)[DPP][PDI]$
$n = 2$   $2(4K_1)[DPP]^2 + 2(4K_1)(4K_2)[DPP]^2[PDI] + 2(4K_1)(4K_2)(K_2K_3)[DPP]^2[PDI]^2$
$n = 3$   $3(4K_1)^2[DPP]^3 + 3(4K_1)^2(6K_2)[DPP]^3[PDI] + 3(4K_1)^2(6K_2)(K_2K_3)[DPP]^3[PDI]^2 + 3(4K_1)^2(6K_2)(K_2K_3)^2[DPP]^3[PDI]^3$
$\downarrow$
$n = \infty$ From the equations above, the mass balance equation can be rewritten as:

$$[DPP]_t = [DPP] \sum_{n=1}^{\infty} \left( n(4K_1[DPP])^{n-1} \left( 1 + 2nK_2[PDI] \sum_{i=0}^{n-1} (K_2K_3[PDI])^i \right) \right) \quad (17)$$

Using relationship 18, equation 17 can be re-written as equation 19.

$$\sum_{i=0}^{n-1} x^i = \frac{1 - x^n}{1 - x} \quad (18)$$

$$[DPP]_t = [DPP] \sum_{n=1}^{\infty} \left( n(4K_1[DPP])^{n-1} \left( 1 + \frac{2nK_2[PDI] - 2nK_2^{n+1}K_3^n[PDI]^{n+1}}{1 - K_2K_3[PDI]} \right) \right) \quad (19)$$

Expanding Equation 19 gives Equation 20, which can be solved using Equations 9 and Equation 21 to give Equation 22.

$$[DPP]_t = [DPP]\sum_{n=1}^{\infty} n(4K_1[DPP])^{n-1} + \tag{20}$$

$$\frac{2K_2[PDI][DPP]}{1-K_2K_3[PDI]}\sum_{n=1}^{\infty} n^2(4K_1[DPP])^{n-1} -$$

$$\frac{2K_2^2 K_3[PDI]^2[DPP]}{1-K_2K_3[PDI]}\sum_{n=1}^{\infty} n^2(4K_1K_2K_3[PDI][DPP])^{n-1}$$

$$\sum_{n=1}^{\infty} n^2 x^{n-1} = \frac{1+x}{(1-x)^3} \tag{21}$$

$$0 = -[DPP]_t + \frac{[DPP]}{(1-4K_1[DPP])^2} + \tag{22}$$

$$\frac{2K_2[PDI][DPP] + 8K_1K_2[PDI][DPP]^2}{(1-K_2K_3[PDI])(1-4K_1[DPP])^3} -$$

$$\frac{2K_2^2 K_3[PDI]^2[DPP] + 8K_1K_2^2 K_3^2[PDI]^3[DPP]^2}{(1-K_2K_3[PDI])(1-4K_1K_2K_3[PDI][DPP])^3}$$

For $[PDI]_t$:

$n = 1 \quad [(DPP)(PDI)]$
$n = 2 \quad [(DPP)_2(PDI)] + 2[(DPP)_2(PDI)_2]$
$n = 3 \quad [(DPP)_3(PDI)] + 2[(DPP)_3(PDI)_2] + 3[(DPP)_3(PDI)_3]$
$\downarrow$
$n = \infty$ Substituting in equations 14-16 give:

For $[PDI]_t$:

$n = 1 \quad (2K_2)[DPP][PDI]$
$n = 2 \quad (4K_1)(4K_2)[DPP]^2[PDI] + 2(4K_1)(4K_2)(K_2K_3)[DPP]^2[PDI]^2$
$n = 3 \quad (4K_1)^2(6K_2)[DPP]^3[PDI] + 2(4K_1)^2(6K_2)$
$\quad\quad\quad (K_2K_3)^2[DPP]^3[PDI]^2 + 3(4K_1)^2(6K_2)(K_2K_3)^2[DPP]^3[PDI]^3$
$\downarrow$
$n = \infty$ From the equations above, the mass balance equation can be rewritten as:

$$[PDI]_t = [PDI] + 2K_2[PDI][DPP] \tag{23}$$

$$\sum_{n=1}^{\infty}\left((n(4K_1[DPP])^{n-1})\left(\sum_{i=0}^{n-1}((i+1)(K_2K_3[PDI])^i)\right)\right)$$

Using relationship 24, equation 23 can be re-written as equation 25.

$$\sum_{i=0}^{n-1}(i+1)x^i = \frac{1-(n+1)x^n + nx^{n+1}}{(1-x)^2} \tag{24}$$

$$[PDI]_t = [PDI] + \frac{2K_2[PDI][DPP]}{(1-K_2K_3[PDI])^2} \tag{25}$$

$$\sum_{n=1}^{\infty}\left((n(4K_1[DPP])^{n-1})\binom{1-(n+1)(K_2K_3[PDI])^n +}{n(K_2K_3[PDI])^{n+1}}\right)$$

Expanding Equation 25 gives Equation 26, which can be solved using Equations 9 and Equation 21 to give Equation 27.

$$[PDI]_t = [PDI] + \frac{2K_2[PDI][DPP]}{(1-K_2K_3[PDI])^2}\sum_{n=1}^{\infty} n(4K_1[DPP])^{n-1} + \tag{26}$$

$$\frac{2K_2^3 K_3^2[PDI]^3[DPP] - 2K_2^2 K_3[PDI]^2[DPP]}{(1-K_2K_3[PDI])^2}$$

$$\sum_{n=1}^{\infty} n^2(4K_1K_2K_3[PDI][DPP])^{n-1} -$$

$$\frac{2K_2^2 K_3[PDI]^2[DPP]}{(1-K_2K_3[PDI])^2}\sum_{n=1}^{\infty} n(4K_1K_2K_3[DPP][PDI])^{n-1}$$

$$0 = -[PDI]_t + [PDI] + \frac{2K_2[PDI][DPP]}{(1-K_2K_3[PDI])^2(1-4K_1[DPP])^2} + \tag{27}$$

$$\frac{(2K_2^3 K_3^2[PDI]^3[DPP] - 2K_2^2 K_3[PDI]^2[DPP])}{(1-K_2K_3[PDI])^2(1-4K_1K_2K_3[PDI][DPP])^3} -$$

$$\frac{2K_2^2 K_3[PDI]^2[DPP]}{(1-K_2K_3[PDI])^2(1-4K_1K_2K_3[PDI][DPP])^2}$$

Equations 22 and 27 can be expressed as two multivariable functions 28 and 29:

$$f([PDI],[DPP]) = -[DPP]_t + \frac{[DPP]}{(1-4K_1[DPP])^2} + \tag{28}$$

$$\frac{2K_2[PDI][DPP] + 8K_1K_2[PDI][DPP]^2}{(1-K_2K_3[PDI])(1-4K_1[DPP])^3} -$$

$$\frac{2K_2^2 K_3[PDI]^2[DPP] + 8K_1K_2^2 K_3^2[PDI]^3[DPP]^2}{(1-K_2K_3[PDI])(1-4K_1K_2K_3[PDI][DPP])^3}$$

$$g([PDI],[DPP]) = \tag{29}$$

$$-[PDI]_t + [PDI] + \frac{2K_2[PDI][DPP]}{(1-K_2K_3[PDI])^2(1-4K_1[DPP])^2} +$$

$$\frac{(2K_2^3 K_3^2[PDI]^3[DPP] - 2K_2^2 K_3[PDI]^2[DPP])}{(1-K_2K_3[PDI])^2(1-4K_1K_2K_3[PDI][DPP])^3} -$$

$$\frac{2K_2^2 K_3[PDI]^2[DPP]}{(1-K_2K_3[PDI])^2(1-4K_1K_2K_3[PDI][DPP])^2}$$

Thus, at any given value of $K_3$, $K_4$, $K_5$, $[DPP]_t$, and $[PDI]_t$, equations 28 and 29 can be iteratively converged unto $f([PDI],[DPP])=g([PDI],[DPP])=0$, giving [PDI] and [DPP]. Accordingly, Newton's Method was implemented in Microsoft Excel with each two columns corresponding to an iteration of Equation 28 and 29:

$$[PDI]_{n+1} = [PDI]_n - \frac{f([PDI]_n)}{\partial_{[PDI]} f([PDI]_n)} \quad [DPP] = [DPP]_n$$

-continued $$[DPP]_{n+1} = [DPP]_n - \frac{g([DPP]_n)}{\partial_{[DPP]} g([DPP]_n)} \quad [PDI] = [PDI]_{n+1}$$

$$[PDI]_{n+2} = [PDI]_{n+1} - \frac{f([PDI]_{n+1})}{\partial_{[PDI]} f([PDI]_{n+1})} \quad [DPP] = [DPP]_{n+1}$$

$$[DPP]_{n+2} = [DPP]_{n+1} - \frac{g([DPP]_{n+1})}{\partial_{[DPP]} g([DPP]_{n+1})} \quad [PDI] = [PDI]_{n+2}$$

And so forth until convergence is obtained.

To calculate the theoretical UV/Vis and CD data for the fitting, it was assumed that any two or more molecules of PDI acceptor 3 in the π•••π stacks will contribute to the absorbance band at 615 nm with each residue exhibiting a temperature independent extinction coefficient ($\epsilon_2$). All molecules of PDI acceptor 3 in any other state, including monomers and heteroaggregates with only one molecule of PDI acceptor 3, exhibits a different extinction coefficient ($\epsilon_1$), which is equivalent to the initial absorbance observed at 615 nm prior to the onset of hetero aggregation.

All heteroaggregates with one molecule of PDI acceptor 3 can be expressed by equation 30, which can be solved using equation 7 to yield equation 31:

$$\sum_{n=1}^{\infty} [(DPP)_n(PDI)] = 2K_2[DPP][PDI] \sum_{n=1}^{\infty} n(4K_1[DPP])^{n-1} \quad (30)$$

$$\sum_{n=1}^{\infty} [(DPP)_n(PDI)] = \frac{2K_2[DPP][PDI]}{(1 - 4K_1[DPP])^2} \quad (31)$$

Thus, the theoretical absorbance can be calculated as:

$$A = \left([PDI] + \frac{2K_2[DPP][PDI]}{(1 - 4K_1[DPP])^2}\right)\epsilon_1 + \left([PDI]_t - [PDI] - \frac{2K_2[DPP][PDI]}{(1 - 4K_1[DPP])^2}\right)\epsilon_2 \quad (32)$$

Since the transition temperature for CD is significantly less than that observed by UV/Vis, it was assumed that monomers and heteroaggregates containing either one or two molecules of PDI acceptor 3 yield no signal. That is, at the very minimum, three molecules of 3 need to be π•••π stacked to obtain an ordered aggregate. The total concentration of all aggregates containing two bound PDI molecules can be expressed as:

$$\sum_{n=1}^{\infty} [(DPP)_n(PDI)_2] = \quad (33)$$
$$2(4K_1)(2K_2)(K_2K_3)[DPP]^2[PDI]^2 \sum_{n=1}^{\infty} (n+1)(4K_1K_2K_3[DPP])^{n-1}$$

Equation 33 can be solved to give:

$$\sum_{n=1}^{\infty} [(DPP)_n(PDI)_2] = \quad (34)$$
$$\frac{(2(4K_1)(2K_2)(K_2K_3)[DPP]^2[PDI]^2)(1 - 4K_1K_2K_3) + 2(4K_1)(2K_2)(K_2K_3)[DPP]^2[PDI]^2}{(1 - 4K_1K_2K_3)^2}$$

Thus, the CD signal can be calculated as:

$$CD = \left(\frac{[PDI]_t - [PDI] - \frac{2K_2[DPP][PDI]}{(1 - 4K_1[DPP])^2}}{(2(4K_1)(2K_2)(K_2K_3)[DPP]^2[PDI]^2)(1 - 4K_1K_2K_3) + \frac{2(4K_1)(2K_2)(K_2K_3)[DPP]^2[PDI]^2}{(1 - 4K_1K_2K_3)^2}}\right)X \quad (35)$$

Where X is a proportionality constant.

To fit the variable temperature UV/Vis and CD spectra, $K_a$s are generated from the van't Hoff equation (Equation 10) and are then used to calculate the hypothetical absorbance and CD at each temperature (Equation 19). The theoretical data is then fitted to the experimental UV/Vis and CD data simultaneously by minimizing the SSR (Equation 1) using the thermodynamic parameters ($\Delta H°$ and $\Delta S°$), the extinction coefficients, and CD proportionality constant as fitting parameters.

4. Variable Temperature UV/Vis Spectra

General Methods

Figure 7:
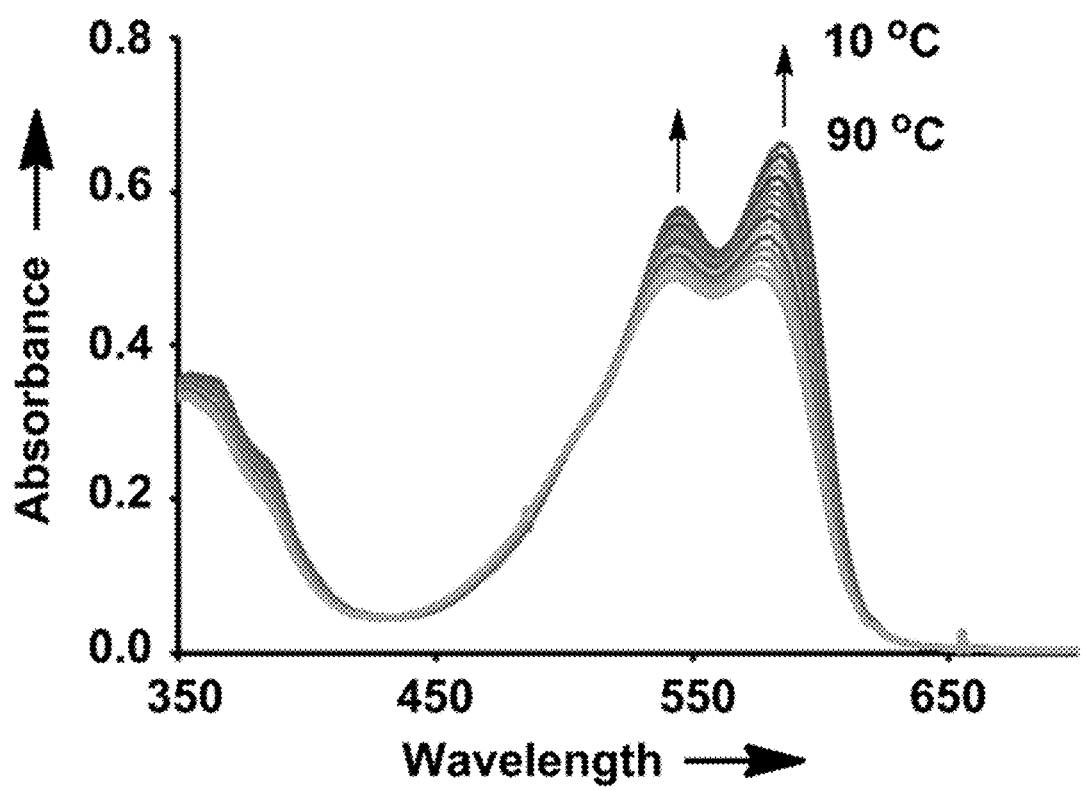
FIG. 7. Variable temperature UV/Vis of an 18.0 µM solution of DPP donor 2 in toluene.
Figure 8:
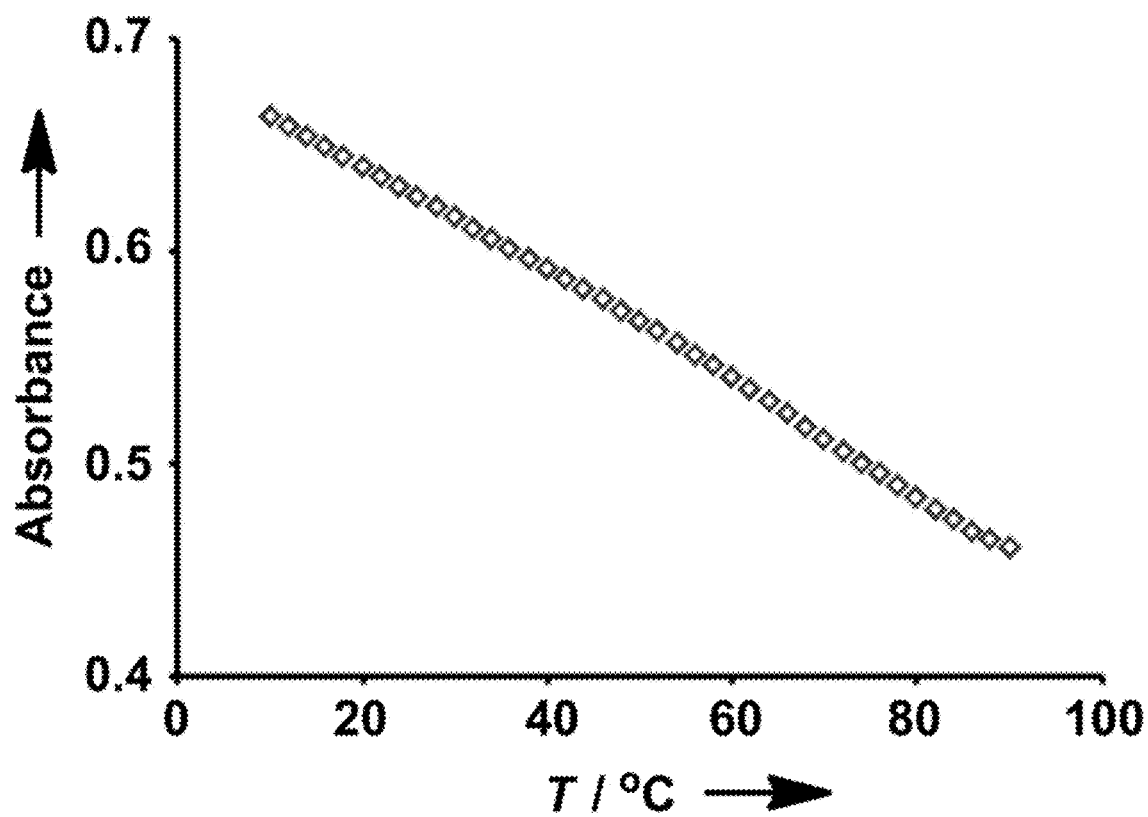
FIG. 8. The absorbance at 584 nm of a 18.0 µM solution of DPP donor 2 in toluene versus sample temperature. Note a fully aggregated or disaggregated state is never reached.
Figure 9:
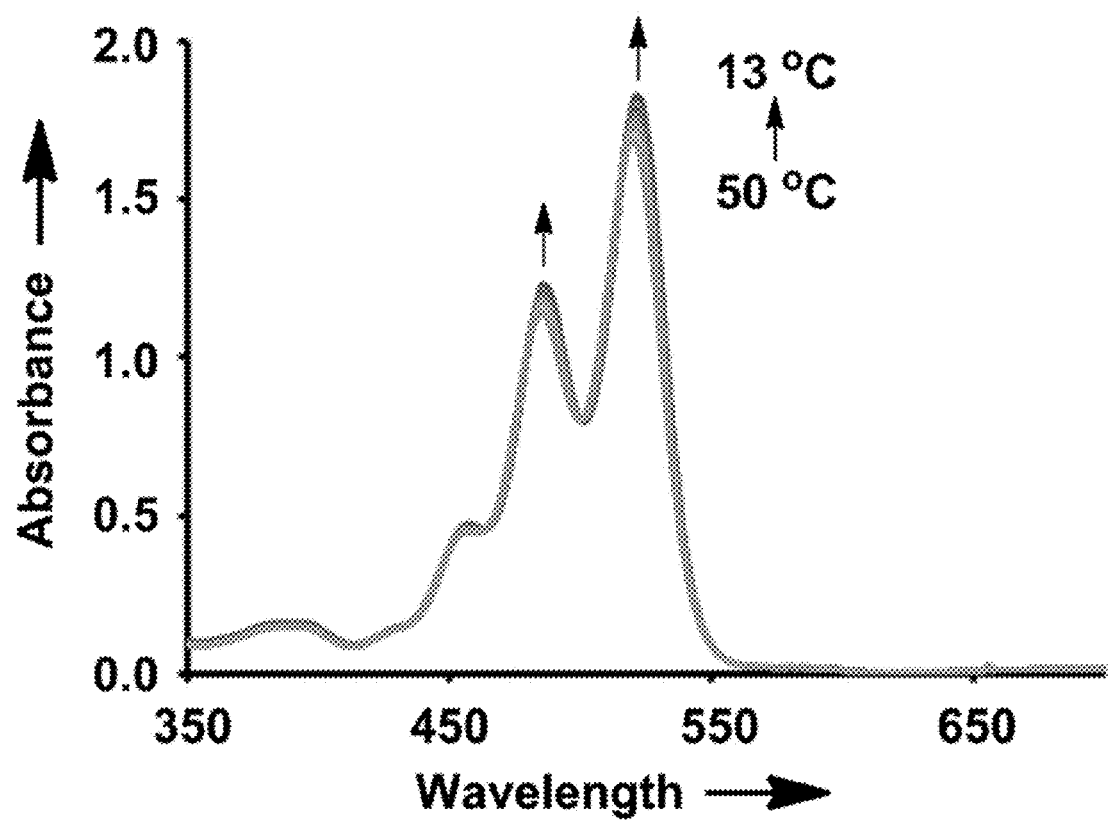
FIG. 9. Variable temperature UV/Vis of a 70 µM solution of 13 in toluene.
Figure 10:
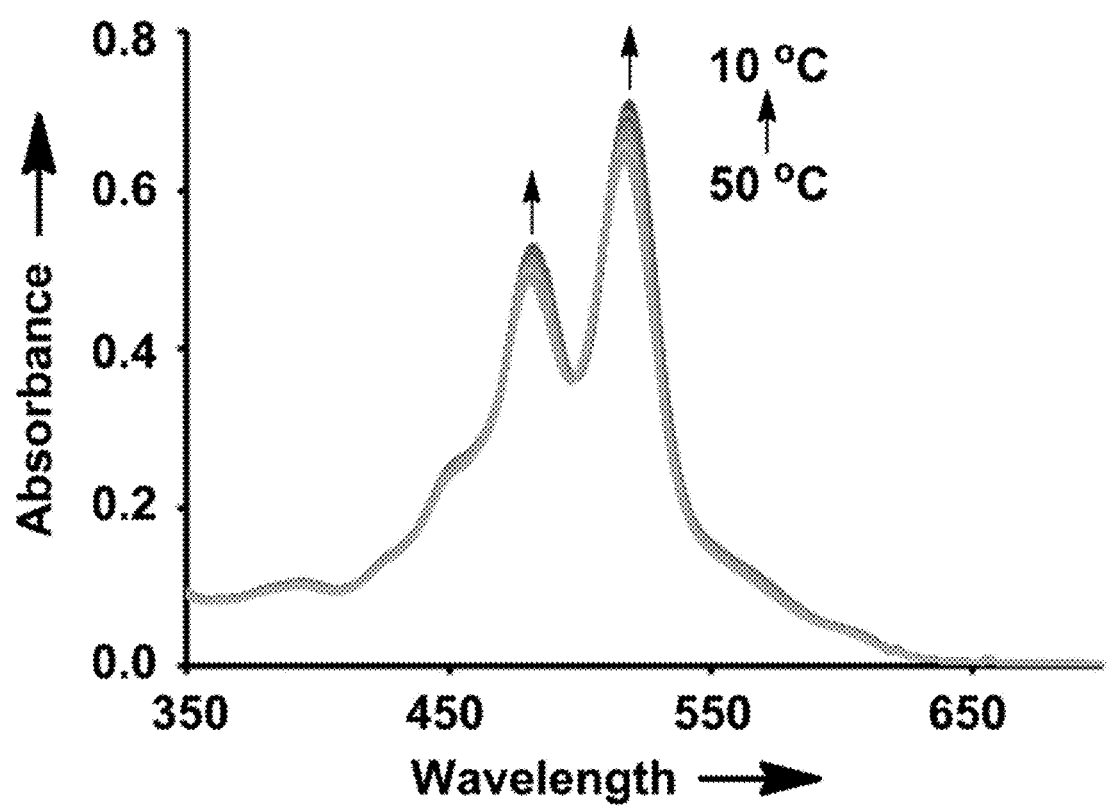
FIG. 10. Variable temperature UV/Vis of a 35.0 µM solution of PDI acceptor 3 in 97:3 toluene:DMSO.
Figure 11:
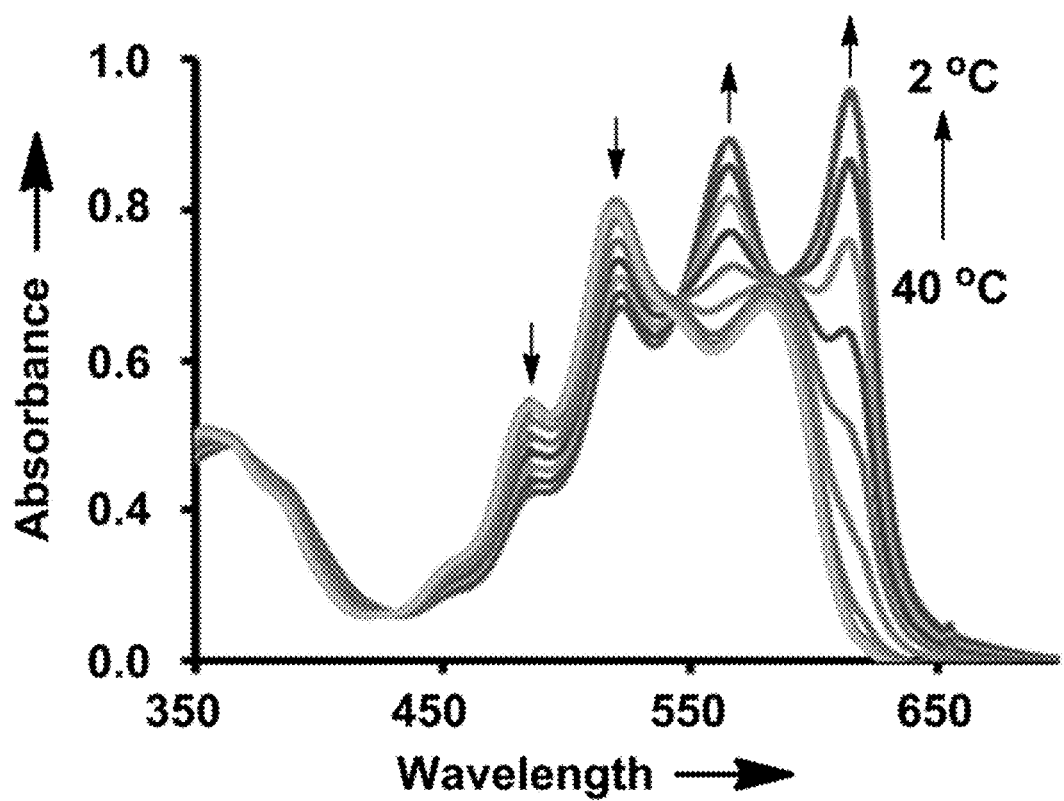
FIG. 11. Variable temperature UV/Vis of a mixture of 2 (70 µM) and 3 (35 µM) in toluene.

UV/Vis measurements were performed on an Agilent 8453 spectrophotometer equipped with a temperature control accessory. For all measurements, the temperatures were corrected using an external digital thermometer with a microprobe accessory. Quartz cuvettes with 1 cm path lengths were used. All samples were prepared with dried solvents in volumetric glassware and were heated within the cell holder at the highest measured temperature (e.g. 50 or 90° C.) for 30 min prior to cooling/measurement to ensure disaggregation. For each variable temperature experiment, increments of 1 or 2° C. were performed with a 10 minute equilibration time between each measurement. FIG. 7 illustrates variable temperature UV/Vis of an 18.0 μM solution of DPP donor 2 in toluene. FIG. 8 illustrates the absorbance at 584 nm of a 18.0 μM solution of DPP donor 2 in toluene versus sample temperature. Note a fully aggregated or disaggregated state is never reached. FIG. 9 illustrates variable temperature UV/Vis of a 70 μM solution of 13 in toluene. FIG. 10 illustrates variable temperature UV/Vis of a 35.0 μM solution of PDI acceptor 3 in 97:3 toluene:DMSO. FIG. 11 illustrates variable temperature UV/Vis of a mixture of 2 (70 μM) and 3 (35 μM) in toluene.

5. Computational Methods

DFT Calculations of geometries, energies, and structural properties were performed with Gaussian 09. Donor and acceptor geometries were optimized using Becke's three parameter exchange functional combined with the Lee-Yang-Parr correlation functional (B3LYP), and the 6-31G(d,p) basis set on an ultrafine grid using tight convergence criteria. Minimization of structure was confirmed via frequency calculations and all structures were found to be minimum energy structures. Enthalpies of H-bonding and π•••π stacking were calculated from converged fragments at the B3LYP/6-31G(d, p) level of theory with identical grid and convergence criteria. The length of the alkyl chains within 1 and 3 were reduced for speed of calculation.

Figure 12:
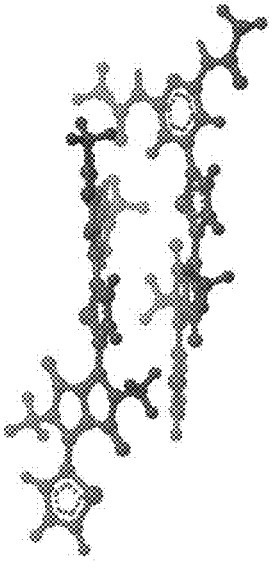
FIG. 12. Structures of the different supramolecular aggregates formed in the titration experiments as calculated at the B3LYP/6-31G(d,p) level of theory, with the corresponding calculated enthalpies of binding.
Figure 12:
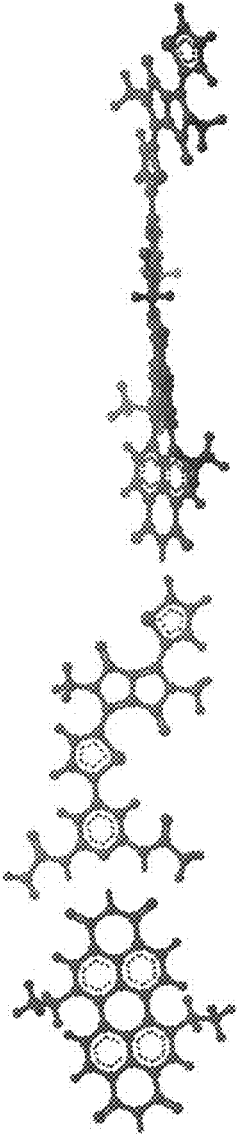
Figure 12:
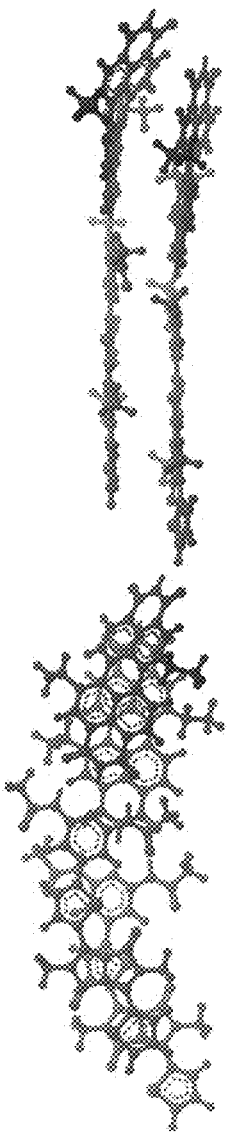

FIG. 12 shows computed structures of the different supramolecular aggregates formed in the titration experiments, with the corresponding calculated enthalpies of binding.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A self-assemblying composition comprising:
a plurality of diketopyrrolepyrrole donors having at least two solubilizing alkyl side chains (R1); and
a plurality of perylenediimide acceptors;
wherein each of the plurality of diketopyrrolepyrrole donors triple hydrogen-bonds along a first spatial axis (x) with one of the plurality of perylenediimide acceptors and each of the plurality of diketopyrrolepyrrole donors interacts with another of the plurality of diketopyrrolepyrrole donors via π•••π stacking along a second spatial axis (z) orthogonal to the first spatial axis (x), each of the plurality of perylenediimide acceptors interacts with another of the plurality of perylenediimide acceptors via π•••π stacking along the second spatial axis (z) orthogonal to the first spatial axis (x),and the solubilizing alkyl chains extending along a third spatial axis (y) orthogonal to the first spatial axis and the second spatial axis.

2. The self assembling composition of claim 1, wherein the composition is chiral.

3. The self assembling composition of claim 1, further comprising a 2 to 1 ratio of the plurality of diketopyrrole donors to the plurality of perylenediimide acceptors.

4. A self-assemblying composition comprising:
a plurality of diketopyrrolepyrrole donors having a structure of:

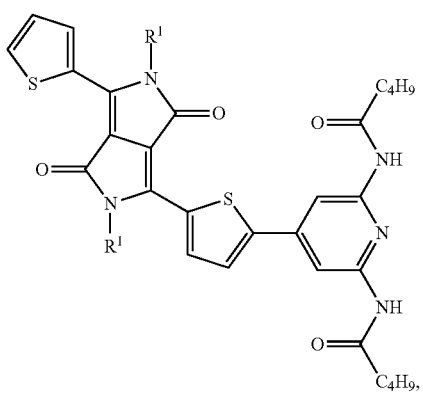

where $R_1$ is an alkyl group; and
a plurality of perylenediimide acceptors, having the structure of:

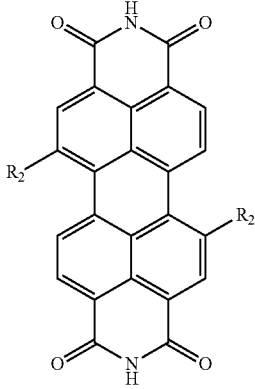

where $R_2$ is an alkyl group;
wherein each of the plurality of diketopyrrolepyrrole donors interacts with another of the plurality of diketopyrrolepyrrole donors via π•••π stacking and noncovalently interacts with one of the plurality of perylenediimide acceptors.

5. The self assembling composition of claim 4, wherein the composition is chiral.

6. The self assembling composition of claim 4, further comprising a 2 to 1 ratio of diketopyrrole donors to perylenediimide acceptors.

7. The self assembling composition of claim 4, wherein the π•••π stacking is along a first axis and the noncovalent interaction is along a second axis.

8. The self assembling composition of claim 4, wherein R2 groups of the plurality of perylenediimide acceptors have a structure of:

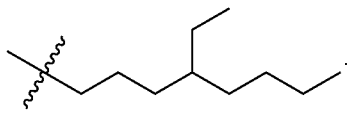 [SMILES: *CCCC(CC)CCCC]

9. The self assembling composition of claim 4, wherein R1 groups of the plurality of diketopyrrolepyrole donors are selected from the group consisting of:
racemic 2-ethyloctyl of the general structure

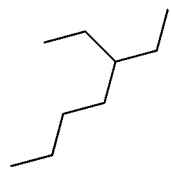

and homochiral (S)-2-methylbutyl of the general structure

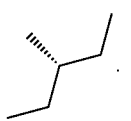

* * * * *